United States Patent [19]
Darrow et al.

[11] Patent Number: 5,671,739
[45] Date of Patent: Sep. 30, 1997

[54] IMAGING OF INTERVENTIONAL DEVICES DURING MEDICAL PROCEDURES

[75] Inventors: Robert David Darrow, Scotia; Charles Lucian Dumoulin, Ballston Lake, both of N.Y.; Steven Peter Souza, Williamstown, Mass.

[73] Assignee: General Electric Company, Schenectady, N.Y.

[21] Appl. No.: 698,700

[22] Filed: Aug. 16, 1996

Related U.S. Application Data

[62] Division of Ser. No. 415,409, Apr. 3, 1995, Pat. No. 5,577,502.

[51] Int. Cl.$^6$ .................................................. A61B 5/055
[52] U.S. Cl. .............................. 128/653.1; 128/721
[58] Field of Search ........................ 128/653.1, 653.2, 128/721, 897–899; 378/41, 42, 62, 63

[56] References Cited

U.S. PATENT DOCUMENTS

| | | |
|---|---|---|
| 4,694,836 | 9/1987 | Buikman et al. |
| 4,930,508 | 6/1990 | Shimoni et al. |
| 5,211,165 | 5/1993 | Dumoulin et al. |
| 5,251,629 | 10/1993 | Koizumi et al. |
| 5,251,635 | 10/1993 | Dumoulin et al. |
| 5,255,680 | 10/1993 | Darrow et al. |
| 5,265,610 | 11/1993 | Darrow et al. |
| 5,271,400 | 12/1993 | Dumoulin et al. |
| 5,307,808 | 5/1994 | Dumoulin et al. |
| 5,318,025 | 6/1994 | Dumoulin et al. |
| 5,377,678 | 1/1995 | Dumoulin et al. |
| 5,482,042 | 1/1996 | Fujita. |
| 5,586,201 | 12/1996 | Whiting et al. |

*Primary Examiner*—Marvin M. Lateef
*Assistant Examiner*—Shawna J. Shaw
*Attorney, Agent, or Firm*—Lawrence P. Zale; Marvin Snyder

[57] ABSTRACT

A tracking system monitors the position of a device within a subject and superimposes a graphic symbol on a diagnostic image of the subject. Registration of the tracked location with the diagnostic image is maintained in the presence of subject motion by monitoring subject motion and adjusting the display to compensate for subject motion. Motion monitoring can be performed with ultrasonic, optical or mechanical methods. The display can be adjusted by modifying the displayed location of the device or it can be adjusted by translating, rotating or distorting the diagnostic image.

11 Claims, 3 Drawing Sheets

IMAGING OF INTERVENTIONAL DEVICES DURING MEDICAL PROCEDURES

CROSS REFERENCE TO RELATED PENDING APPLICATIONS

The present application is a divisional of "IMAGING OF INTERVENTIONAL DEVICES DURING MEDICAL PROCEDURES" by Darrow, Dumoulin, Souza, Ser. No. 08/415,409, filed Apr. 3, 1995 now U.S. Pat. No. 5,577,502 issued Nov. 26, 1996; which was subject to a Restriction Requirement; and is related to co-pending U.S. patent application "IMAGING OF INTERVENTIONAL DEVICES IN A NON-STATIONARY SUBJECT" by Darrow, Dumoulin, Souza Ser. No. 08/415,410. This is also related to "TRACKING SYSTEM TO MONITOR THE POSITION AND ORIENTATION OF A DEVICE USING MAGNETIC RESONANCE DETECTION OF A SAMPLE CONTAINED WITHIN THE DEVICE" by Dumoulin, Souza, Darrow U.S. Pat. No. 5,271,400 issued Dec. 21, 1993.

FIELD OF THE INVENTION

The present invention relates to medical procedures in which a device is inserted into a body, and more particularly concerns tracking of such a device with magnetic resonance signals or with radio-frequency localization.

DESCRIPTION OF RELATED ART

X-ray fluoroscopes are routinely used to track the insertion of interventional devices in a subject during diagnostic and therapeutic procedures. Fluoroscopes irradiate the subject with X-ray radiation at regular intervals to obtain a series of images of the subject. Conventional X-ray fluoroscopes are designed to minimize X-ray dosage. Nevertheless, some procedures can be very long and the accumulated X-ray dose to the subject can become significant. The long term exposure of the attending medical staff is of even greater concern since they participate in these procedures regularly. Consequently, it is desirable to reduce or eliminate the X-ray dose during these procedures.

Another limitation on the use of X-ray fluoroscopes is that the technique is projective in nature and produces a single two-dimensional image. Information concerning the depth of an object within the field-of-view is not available to a physician. It is often desirable to obtain this information during surgical procedures.

Several method of using radio frequency (RF) signals to track a device in a subject have been disclosed in U.S. Pat. No. 5,211,165 May 18, 1993 "Tracking System To Monitor The Position And Orientation Of A Device With Radiofrequency Field Gradients" by C. Dumoulin, R. Darrow, J. Schenck and S. Souza; U.S. Pat. No. 5,377,678 Jan. 3, 1995 "Tracking System To Monitor The Position And Orientation Of A Device With Radiofrequency Fields" by C. Dumoulin, R. Darrow, J. Schenck and P. Roemer; U.S. Pat. No. 5,251,635 Oct. 12, 1993 "Stereoscopic X-Ray Fluoroscopy System Using Radiofrequency Fields" by C. Dumoulin and R. Darrow; U.S. Pat. No. 5,255,680 Oct. 26, 1993 "Automatic Gantry Positioning For Imaging Systems" by R. Darrow and C. Dumoulin; and U.S. Pat. No. 5,265,610 Nov. 30, 1993 "Multi-Planar X-Ray Fluoroscopy System Using Radiofrequency Fields" by R. Darrow and C. Dumoulin, assigned to the present assignee, and hereby incorporated by reference. These methods do not require the use of X-rays but employ RF transmitting and receiving apparatus to track a device in a body.

Several methods for tracking devices within a subject employing magnetic resonance (MR) have been disclosed in U.S. patent application Ser. No. 07/861,662 filed Apr. 1, 1992 now U.S. Pat. No. 5,271,400 filed Dec. 21, 1993; "Tracking System To Monitor The Position And Orientation Of A Device Using Magnetic Resonance Detection Of A Sample Contained Within The Device"; U.S. Pat. No. 5,307,808 May 3, 1994 "Tracking System And Pulse Sequences To Monitor The Position Of A Device Using Magnetic Resonance" and U.S. Pat. No. 5,318,025 Jun. 7, 1994 "Tracking System To Monitor The Position And Orientation Of A Device Using Multiplexed Magnetic Resonance Detection" all by Charles L. Dumoulin, Steven P. Souza and Robert Darrow, all assigned to the present assignee, and all hereby incorporated by reference. The MR imaging system does not pose the hazards of ionizing X-rays to the subject and medical staff as does X-ray imaging.

RF and MR methods of tracking an interventional device provide a real-time display of device location which is superimposed upon a static diagnostic image. As long as the subject remains stationary, the displayed location of the device superimposed upon the reference image is accurate. If the subject moves after the acquisition of the reference image, the displayed location of the device will be incorrectly registered with the reference image.

Currently, there is a need for a system for tracking a device within a non-stationary subject and providing a correctly registered image of the tracked device and subject.

SUMMARY OF THE INVENTION

The position/orientation of an interventional device within a subject is tracked and used to provide a correctly registered representation of the device on a reference image of a non-stationary subject.

A reference image of the subject is acquired with an imaging device and position/orientation of the subject is monitored with ultrasonic, optical or mechanical detectors at the time of image acquisition.

The change in position of selected points of the subject between image acquisition and device location measurement are determined.

These positional changes are used to translate, rotate and/or distort the reference image, or the computed position of the interventional device to improve registration of the displayed device location with the acquired image.

OBJECTS OF THE INVENTION

It is an object of the present invention to provide a method for the compensation of subject motion during tracking of an interventional device.

It is another object of the present invention to provide a system for tracking a device within a non-stationary subject minimizing the amount of image acquisition required.

It is another object of the present invention to reduce the amount of ionizing radiation required to track an interventional device within a subject.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Typically, in conventional tracking systems, the location of an interventional device is presented to a physician as a graphic symbol superimposed upon a diagnostic image. Due to time constraints, or the constraint of accumulated radiation dose, diagnostic images are acquired intermittently before tracking of the device commences, or are acquired at a much slower rate that the device is tracked. Consequently, if the subject moves after the acquisition of the diagnostic image, the representation of the device displayed to the physician may be misregistered with respect to the diagnostic image.

In the present invention, this problem is overcome by monitoring subject motion. In the event that motion is detected, the present invention responds to, and corrects for the subject motion.

Figure 1:
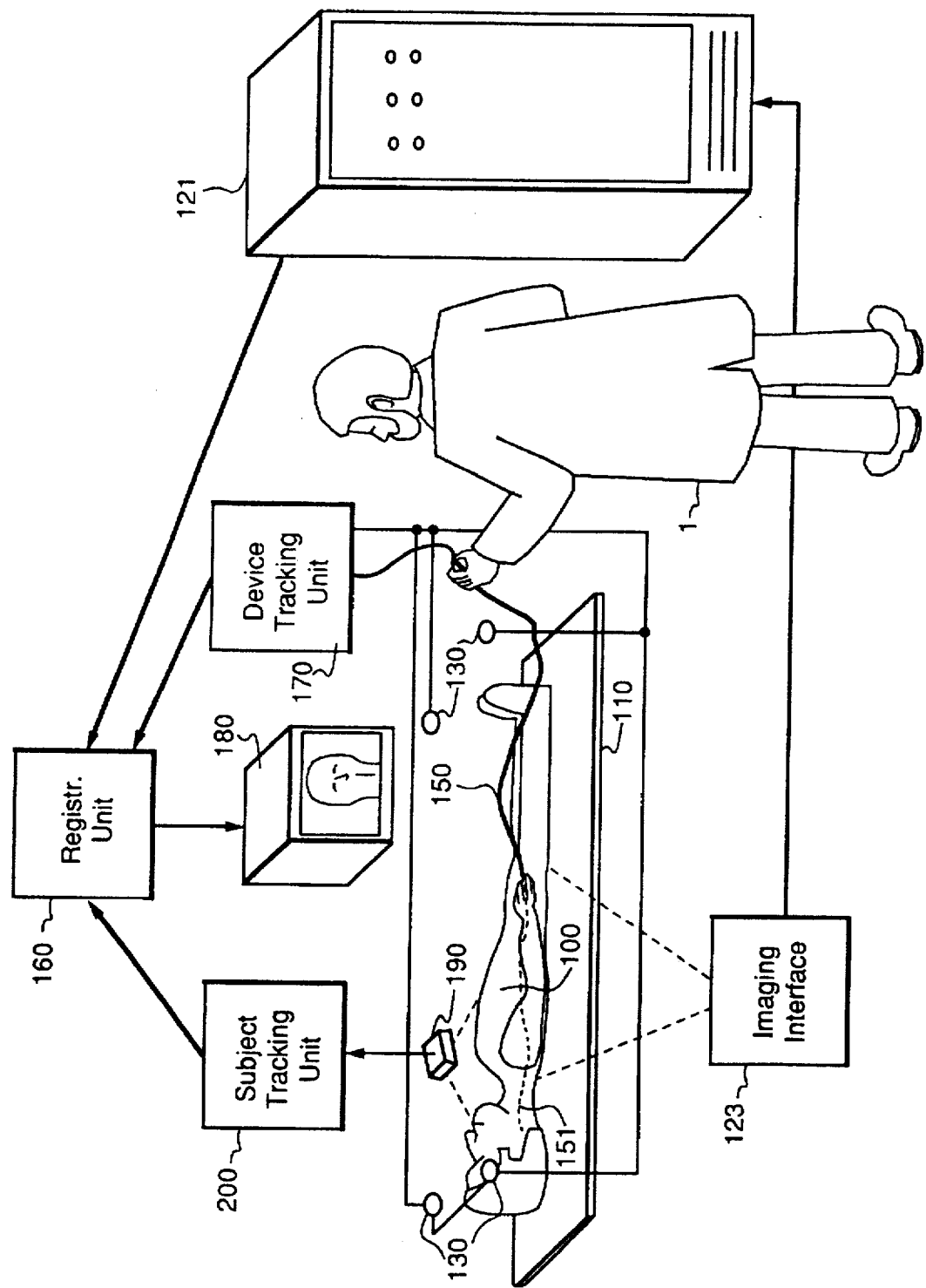
FIG. 1 is a perspective view of an embodiment of the present invention in operation tracking the location of a device in a subject.

In FIG. 1, a subject 100 on a support table 110 is placed in an imaging device 120, having imaging interface 123 and imaging electronics 121, collectively referred to as imaging device 120. Imaging device 120 may be an X-Ray imaging device, a computed tomography (CT) scanner, Positron Emission Tomography system or ultrasound scanner, or any other conventional medical imaging device. An invasive device 150, shown in FIG. 1 as a catheter, is inserted into subject 100, usually by physician 1. Device 150 may be a guide wire, a catheter, an endoscope, a laparoscope, a biopsy needle or similar device.

Device 150 contains one or more element(s) 151, which may be easily tracked. For example, in an MR imaging device, it may be an RF coil which detects MR signals generated in subject 100. The element may also be an MR active substance such as a Fluorine compound which is tracked by MR Imaging. In the case of RF tracking, it may be an RF coil tracked by external RF coils 130.

Device tracking unit 170 determines the position of element 151 on device 150 relative to a fixed reference point, such as support table 110.

In the case of RF tracking, the location of device 150 is determined by employing several external detection devices, such as RF coils 130 around the perimeter of subject 100, and at least one internal coil of element 151 attached to device 150. The internal coil transmits RF energy which is received by the external RF coils 130 which are connected to device tracking unit 170. Device tracking unit 170 calculates the position of the internal coil over time. The transmission may be reversed such that external coils 130 transmit RF energy and internal coil of element 151 receives the transmitted RF energy.

In the case of MR tracking, element 151 detects nutation of magnetic resonance in a localized region around element 151. Imaging electronics 121 determines the location of element 151.

If more than one coil is used in element 151, determining the locations of all coils will also allow calculation of the orientation of device 150.

A position detection means 190, placed within the imaging device 120, measures position of one or more reference points of subject 100 over time. A reference image of the subject is acquired by the imaging device 120 at a time $t_i$, and the position of the reference points of subject 100 are monitored by position detection device 190 at this time. The image and corresponding subject location, and position are stored.

Figure 2:
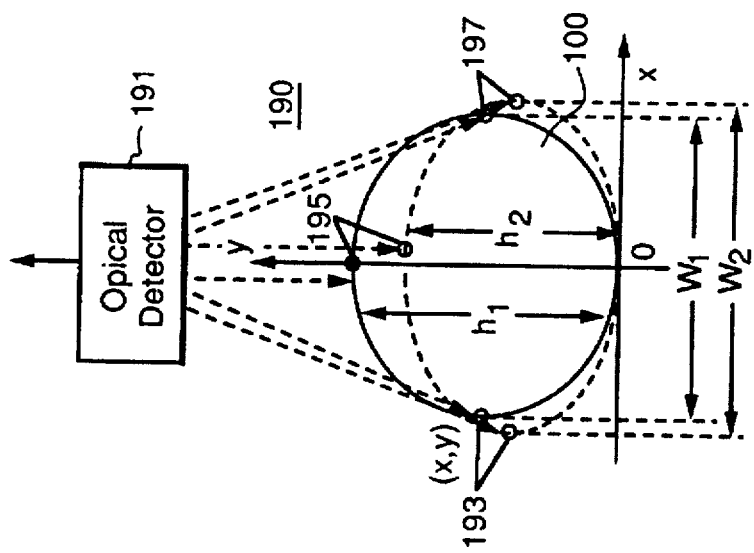
FIG. 2 is an enlarged diagram of an optical embodiment of the position detection means of FIG. 1.

In FIG. 2, position detection means 190 may be comprised of light emitting diodes (LEDs) 193, 195, 197 fixed to subject 100 and an optical detector 191 capable of measuring distance to the LEDs at specified times. This results in a three-dimensional position (x,y,z) of each of the LEDs at any given time t. This positional information is provided to a subject tracking unit 200 of FIG. 1. Using more than one LED allows subject tracking unit 200 to determine both rotational, and translational movement of the subject.

Figure 3:
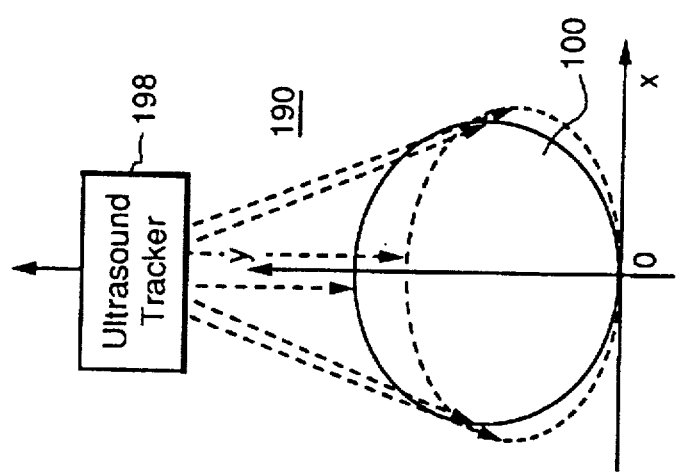
FIG. 3 is an enlarged diagram of an ultrasound embodiment of the position detection means of FIG. 1.

In FIG. 3, an ultrasonic tracking device 198 employs conventional ultrasound distance measurement techniques to determine the position of selected points on subject 100 at different times. This may be employed as position detection means 190.

Figure 4:
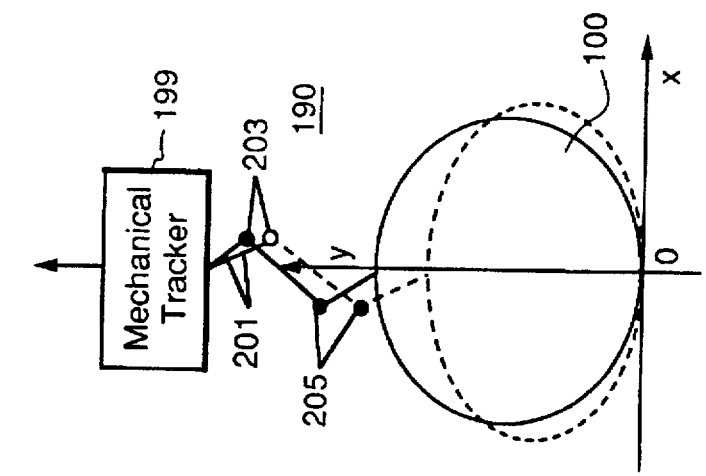
FIG. 4 is an enlarged diagram of a mechanical embodiment of the position detection means of FIG. 1.

In FIG. 4, a mechanical tracking device 199 may also be employed as position detection means 190. It has a mechanical arm 201 physically coupled to subject 100. Sensors 203, 205 in arm 201 physically measures patient position at specified times. Others may be employed to measure the width and height of a portion of the subject's anatomy.

Position information over time from motion detection means 190 is sent to a subject tracking unit 200 for processing. Subject tracking unit 200 computes translation and rotation movement of subject 100 from time $t_i$, the time of image acquisition, to time $t_d$, the time of device location measurement. This movement information is passed to a registration unit 160

Registration unit 160 receives the reference image from imaging device 120, the net subject position and orientation change from subject tracking unit 200, and device 150 position and orientation from device tracking unit 170. Registration unit 160 then translates and rotates the reference image to match the position and orientation of subject 100 at the time the location of device 150 location was measured. An image of device 150, or a graphic symbol of element 151 is synthesized by device tracking unit 170, or by registration unit 160. This image is superimposed upon the translated/rotated image of subject 100 at its absolute location and orientation to result in a registered image having both an image of subject 100 and device 150 correctly registered with each other.

Alternatively, registration unit 160 may transform the absolute location/orientation of device 150 in the reverse sense, then superimpose an image of device 150 at the transformed location/orientation on the reference image.

DEFORMATION OF REFERENCE IMAGE

In addition to translation/rotation of the subject, there is also expansion/contraction of the subject. An image of a cross-section of a subject's chest will expand and contract as the subject breathes. Similarly, an image of the heart within subject 100 will twist and expand/contract during the cardiac cycle. An accurate registration of the reference image and that of a catheter being positioned within the heart is crucial.

In another embodiment, the present invention is adapted to track device 150 during a periodic motion cycle of subject 100. This periodic motion cycle may be a respiratory cycle, or cardiac cycle. In each of these periodic motion cycles, detected expansion of subject 100 can be used to dynamically stretch a single diagnostic image so that physician 1 views a scene which closely approximates the actual dynamics of subject 100. Superposition of a graphic symbol synthesized by either device tracking unit 170, or registration unit 160, upon the dynamically changing diagnostic image provides a more accurate representation of the device's location within subject 100.

One such method is to identify a screen location (x,y) for each pixel of a reference image. The pixel locations are then offset to another location (x',y') to produce a distorted image. This would be particularly useful in viewing a cross-section of subject 100 with a superimposed image of device 150. Device 150 is tracked in relation to fixed coordinates, such as the support table 110. However, as subject 100 breathes, the cross-section changes. The reference image must be distorted, or the position of the image of device 150 must be changed, to provide accurate registration of the images.

Position detection means 190 measures the chest height $h_1$, as shown in FIGS. 2, 3 or 4 of subject 100 at time $t_i$ when the reference image is acquired by imaging device 120. Position detection means 190 measures a second chest height $h_2$ at time $t_d$ when the position of device 150 is determined by device tracking unit 170.

Registration unit 160 receives the reference image acquired at time $t_i$ from imaging electronics 121 of imaging device 120, and the location, position of device 150 at time $t_d$. It also receives the height difference of subject 100 between times $t_i$ and $t_d$, heights $h_1$, $h_2$. Registration unit 160 then performs distortion of the reference image based upon heights $h_1$ and $h_2$.

A one-dimensional approximation would be:

$$y© = y\left(1 - \frac{h_1 - h_2}{h_1}\right) \quad (1)$$

where y' is the distorted location of the pixel previously located at y on the reference image, and $h_1$ is the height at image acquisition, and $h_2$ is the chest height when the device position was measured. This assumes that the subject is not allowed to expand through support table 110, and is fixed at that point. Registration unit 160 calculates each new y' coordinate to produce a distorted image.

The subject width w may also be monitored as shown in FIG. 2 to provide a distortion in a second dimension. Assuming that subject 100 is free to expand and contract on both sides, the coordinate system is set up to have x=0 pertain to the center of expansion (the point which will not move when subject is not translating or rotating, but simply expanding). This should be approximately the center of the cross-section of patient 100. Patient extent in the 'x' direction is measured at least two times, at $t_i$ and $t_d$. The distorted x' coordinates will be:

$$x© = x\left(1 - \frac{w_1 - w_2}{w_1}\right) \quad (2)$$

where x' is the distorted location of the pixel previously located at x on the reference image, and $w_1$ is the width at image acquisition, and $w_2$ is the width when the device position was measured. Registration unit 160 may then calculate new x' coordinates to produce a distorted image having a two-dimensional distortion.

The distorted image, either 1D distorted, or 2D distorted, may then be rotated and translated as a solid body according to translation and rotation determined by position detection means 190.

Figure 5:
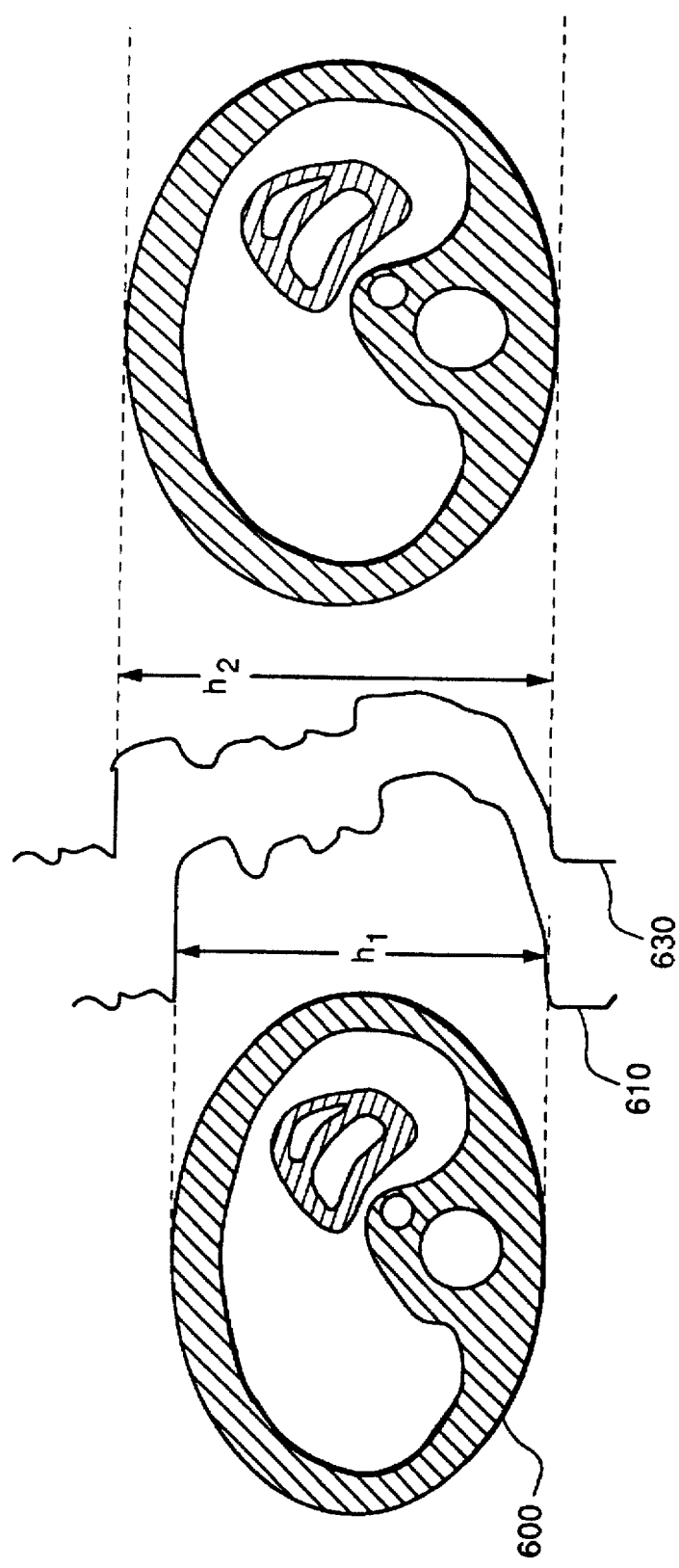
FIG. 5 is a diagram of a two-dimensional magnetic resonance image of a cross-section of a subject and a one-dimensional profile at two different points during the subject's respiratory cycle.

In yet another embodiment of the present invention the MR imaging device may be used in place of position detection unit 190 to detect subject position, orientation, expansion, and contraction. This is illustrated in FIG. 5. In this embodiment, a hue MR image cross-section 600 of subject 100 is shown. A first projection 610 is obtained in a desired direction by applying a slice-selective RF pulse followed by a readout gradient pulse in the desired direction in a manner well known to those skilled in the art. A first projection 610 is employed in determining a first height measurement $h_1$. If subject 100 moves (e.g. inhales), acquisition of a second projection 630 results in a second location and size measurement, $h_2$ which indicates the change in position of subject 100. The change in the detected offset and cross-sectional size of subject 100 is then used to adjust either the displayed location of device 150 or the display of the image.

CINE

Another method of correcting registration of images of a subject having periodic motion is to collect a series of reference images each gated to the periodic motion cycle.

In the case of a respiratory cycle, each image is associated with a measurement of the chest expansion at different times within the respiratory cycle. The chest expansion and device 150 position are measured at time $t_d$. An image, from the series of images, which corresponds to the measured chest expansion at time $t_d$, is selected as the reference image. This reference image is then translated/rotated as described above to provide an updated image of subject 100 at time $t_d$. A representation of the measured location of device 150 at time $t_d$ is superimposed upon the updated image to result in an accurate registered image of subject 100 and device 150.

In the case of a cardiac cycle, a series of images are acquired at different times within the cardiac cycle as measured by an electrocardiogram (EGG) signal.

An ECG signal and device 150 position are measured at time $t_d$. An image, from the series of acquired images, which corresponds to the ECG signal acquired at time $t_d$, is selected as the reference image.

This reference image is then translated/rotated as described above to provide an updated image of subject 100 at time $t_d$. A representation of the measured location of device 150 at time $t_d$ is superimposed upon the updated image to result in an accurate registered image of subject 100 and device 150.

Another method involves playing back the series of images and measuring the device location corresponding to the point of the displayed image within the periodic motion cycle. These images and device locations are used in determining the registered images.

Other responses to motion are possible. The simplest response is to notify physician 1 with an audio or visual alarm and let the physician 1 take appropriate action (such as to acquire another diagnostic image). Alternatively, detection of motion can automatically cause the acquisition of a new diagnostic image.

While several presently preferred embodiments of the novel device have been described in detail herein, many modifications and variations will now become apparent to those skilled in the art. It is, therefore, to be understood that the appended claims are intended to cover all such modifications and variations as fall within the true spirit of the invention.

What is claimed is:

1. A tracking system for monitoring the location of an interventional device within a subject, comprising:

a) imaging means for obtaining at a time $t_i$, a reference image of a subject at a first position and orientation;

b) device tracking means for tracking said device to measure, at time $t_d$, a location of said device and for producing a device image;

c) motion detection means for measuring a net translation and orientation of said subject between time $t_i$, when the reference image was obtained, and time $t_d$ when the device tracking means determines the device location;

d) registration means coupled to the imaging means, the device tracking means, and the motion detection means for translating and rotating the device image relative to the reference image by the net translation and orientation of the subject to enhance registration of the reference image with the tracked device location; and e) display means for displaying the adjusted images.

2. The tracking system recited in claim 1 wherein the imaging means comprises a magnetic resonance imaging system.

3. The tracking system recited in claim 1 wherein the imaging means comprises an X-Ray imaging system.

4. The tracking system recited in claim 1 wherein the device tracking means comprises a magnetic resonance imaging system.

5. The tracking system recited in claim 1 wherein the device tracking means comprises a radio-frequency tracking system.

6. The tracking system recited in claim 1 wherein the device tracking means comprises a magnetic resonance imaging system.

7. The tracking system recited in claim 1 wherein the device tracking means comprises an ultrasound tracking means.

8. The tracking system recited in claim 1 wherein the device tracking means comprises an optical motion detection system.

9. The tracking system recited in claim 1 wherein the device tracking means comprises a mechanical motion detection system.

10. A method for registering tracked locations of a device within a subject with a diagnostic image employing the steps of:

a) measuring translation and rotation of said subject with a motion detection means;

b) correcting said tracking location of said device by subtracting the measured translation and rotation to enhance registration of tracking location with said image.

11. A method for registering a location of a device measured at time $t_d$ within a subject with a diagnostic image acquired at a time $t_i$ employing the steps of:

a) measuring net translation of said subject between time $t_i$ and $t_d$ with a motion detection means;

b) translating said image relative to said location of said device to correct for the measured translation to enhance registration of said image with said tracked device location;

c) measuring net rotation of said subject between time $t_i$ and $t_d$ with a motion detection means; and d) rotating said image relative to said location of said device to correct for the measured rotation to enhance registration of said image with said tracked device location.

* * * * *